United States Patent [19]

Zajacek et al.

[11] 4,052,454

[45] Oct. 4, 1977

[54] PROCESS FOR THE MANUFACTURE OF UREAS

[75] Inventors: John G. Zajacek, Strafford; John J. McCoy, Media, both of Pa.; Karl E. Fuger, Therwil, Switzerland

[73] Assignee: Atlantic Richfield Company, Los Angeles, Calif.

[21] Appl. No.: 674,464

[22] Filed: Apr. 7, 1976

Related U.S. Application Data

[60] Division of Ser. No. 595,474, July 14, 1975, which is a continuation-in-part of Ser. No. 416,158, Nov. 15, 1973, abandoned.

[51] Int. Cl.² .................... C07C 127/19; C07C 127/15
[52] U.S. Cl. ............................ 260/553 A; 260/553 R
[58] Field of Search ....................... 260/553 A, 553 R

[56] References Cited

U.S. PATENT DOCUMENTS

| 2,655,534 | 10/1953 | Searle | 260/553 A |
|---|---|---|---|
| 3,392,197 | 7/1968 | Swakon | 260/553 R |
| 3,539,587 | 11/1970 | Swakon | 260/553 R X |
| 3,636,104 | 1/1972 | Kober et al. | 260/552 R |
| 3,865,875 | 2/1975 | Hearsey et al. | 260/553 R |
| 3,911,006 | 10/1975 | Hearsey | 260/553 A |

FOREIGN PATENT DOCUMENTS

| 203,940 | 9/1955 | Australia | 260/553 A |
|---|---|---|---|
| 634,690 | 1/1962 | Canada | 260/553 A |
| 875,984 | 8/1961 | United Kingdom | 260/553 A |

*Primary Examiner*—Daniel E. Wyman
*Assistant Examiner*—Thomas A. Waltz
*Attorney, Agent, or Firm*—John C. Martin, Jr.

[57] ABSTRACT

A process for the production of ureas by contacting at elevated temperatures and pressures in a basic solution a nitrogenous organic compound containing at least one non-cyclic group, in which a nitrogen atom is directly attached to a single carbon atom and is also attached through a double bond to an oxygen or another nitrogen atom, with carbon monoxide and with water or another nitrogenous organic compound in which the nitrogen atom is directly attached to at least one hydrogen atom, in the presence of an active amount of a catalyst selected from the group consisting of selenium, sulfur, compounds containing selenium, sulfur compounds and mixtures thereof.

12 Claims, No Drawings

PROCESS FOR THE MANUFACTURE OF UREAS

RELATED APPLICATIONS

This is a divisional of application Ser. No. 595,474, filed July 14, 1975, which in turn is a continuation-in-part of application Ser. No. 416,158, filed Nov. 15, 1973, now abandoned.

BACKGROUND OF THE INVENTION

The present invention relates to a process for the manufacture of ureas and, more particularly, to a process for the manufacture of ureas by reaction of a nitrogenous compound having at least one hydrogen atom attached to the nitrogen or water with carbon monoxide and a nitrogenous compound in which the nitrogen is directly attached to a single carbon atom and also is attached through a double bond to an oxygen or another nitrogen under elevated temperatures and pressure conditions in a basic solution and in the presence of a sulfur or selenium catalyst.

Urea and substituted ureas are important intermediates in the preparation of various products, particularly agricultural chemicals useful in soil treatment, as fungicides, insecticides, and germicides, in weed control and other uses. For example 3-(3,4-dichlorophenyl)-1,1-dimethylurea is a preemergence weed control product; 1,1-dimethyl-3-phenylurea is an excellent herbicide; and 3-(p-chlorophenyl)-1,1-dimethylurea is a non-selective weed control product. Thus any method which can be used to produce these and similar ureas is a valuable and useful process.

It is well known in the art to produce ureas by the reaction of an amine compound with an isocyanate or alternatively by the reaction of an amine with phosgene; the reaction chosen is dependent upon the nature of the desired urea. Such processes suffer from a number of disadvantages among which are the necessity for handling toxic and highly reactive compounds, the expense of the starting compounds and the necessity of working in expensive corrosion resistant apparatus resistant to by-product hydrogen chloride generated in the phosgene reaction. Other procedures are available; for example in U.S. Pat. No. 2,877,268 there is described a process for preparing ureas by an apparently noncatalytic reaction of amines with carbonyl sulfide, while British Pat. No. 1,275,702 describes a catalytic process for converting amines to ureas using selenium, carbon monoxide and oxygen. It should be noted that in each of the processes it is an amine that is converted to a urea.

The instant invention is a simple one-step process for the preparation of ureas which eliminates the need for an isocyanate, phosgene, and in one embodiment water is used instead of an amine. Thus it is possible to start with cheaper and more readily available nitrogen-containing organic compounds.

SUMMARY OF THE INVENTION

In accordance with the invention a nitrogenous compound having a nitrogen atom directly attached to a single carbon atom and which is also attached through a double bond to an oxygen atom or another nitrogen atom is contacted with carbon monoxide and a nitrogenous compound having at least one hydrogen atom attached to nitrogen or with water and carbon monoxide in a basic solution at temperatures in the range from 50° to 250° C. under pressures in the range of from 10 atmospheres to 200 atmospheres in the presence of a catalyst that is either selenium, a compound of selenium, sulfur, an inorganic sulfide or an organic sulfide or any combination thereof to produce a urea.

It is an object of the present invention, therefore, to provide an improved process for the production of ureas.

Another object of the present invention is to provide an efficient, one-step process for preparing ureas in high yields by reaction of a nitrogenous compound having a nitrogen atom directly attached to a single carbon atom and which also is attached through a double bond to an oxygen atom or another nitrogen atom with water or a nitrogenous compound in which the nitrogen atom is directly attached to one or more hydrogen atoms and carbon monoxide by using catalytic amounts of either selenium, a compound of selenium, sulfur, an inorganic sulfide or an organic sulfide or any combination thereof.

Another object of the present invention is to provide a process for the production of ureas which uses readily available, low cost starting materials.

Another object of the present invention is to provide a process for the production of ureas which does not require handling toxic and reactive starting materials.

Another object of the present invention is to provide a process for the production of ureas which does not result in the co-production of corrosive hydrogen chloride.

These and other objects of the invention will become apparent from the following description of the process and from the claims.

DESCRIPTION OF THE INVENTION

Suitable nitrogenous compounds containing at least one non-cyclic group in which the nitrogen atom is directly attached to a single carbon atom and is also attached through a double bond to an oxygen or another nitrogen atom typically include such compounds as organic nitro, nitroso, azo, and azoxy compounds generally containing up to 24 carbon atoms. Of these, the organic nitro compounds are generally preferred and the nitro aromatic and tertiary nitroaliphatic compounds are most preferred.

Nitro compounds for use in the process include mononitro compounds such as nitrobenzene, alkyl and alkoxy nitrobenzenes wherein the alkyl group contains up to 10 carbon atoms, aryl and aryloxy nitrobenzenes, wherein the aryl group is phenyl, tolyl, xylyl, naphthyl, chlorophenyl, chlorotolyl, or chloronaphthyl, chloronitrobenzenes such as 4-chloronitrobenzene, 3,4-dichloronitrobenzene, dinitro compounds such as dinitrobenzene, alkyl and alkoxy dinitrobenzenes wherein the alkyl group contains up to 10 carbon atoms, aryl and aryloxy dinitrobenzenes wherein the aryl group is any of those mentioned above, chlorodinitrobenzenes, trinitrocompounds such as trinitrobenzene, alkyl and alkoxy trinitrobenzenes, aryl and aryloxytrinitrobenzenes with the substituents being any of those already mentioned and chlorotrinitrobenzenes as well as similarly substituted mono and polynitro derivatives of the naphthalene, diphenyl, diphenylmethane, anthracene and phenanthracene series as well as nitropyridines.

From this group of nitro compounds the aromatic nitrocompounds such as nitrobenzene, p-nitroanisole, p-nitrophenetole, p-nitrotoluene, 3,4-dichloronitrobenzene, p-chloronitrobenzene, m-chloronitrobenzene, dinitrobenzene, dinitrotoluene, and the tertiary aliphatic nitrocompounds such as 2-methyl-2-nitropropane and 1-methyl-1-nitrocyclohexane are preferred.

Examples of suitable nitrosocompounds are the aromatic nitrosocompounds such as nitrosobenzene, nitrosotoluene and p-chloro-nitrosobenzene.

Suitable azo compounds have the general formula $R_1—N=N—R_2$ wherein $R_1$ and $R_2$ are either the same or different substituted or unsubstituted alkyl or aryl groups selected from among those already listed in the description of suitable nitrocompounds. Azobenzene, chloroazobenzenes and alkyl or aryl substituted azobenzenes are particularly preferred.

Suitable azoxy compounds have the general formula

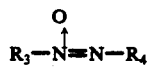

wherein $R_3$ and $R_4$ may be the same or different substituted or unsubstituted alkyl or aryl groups selected from among those already listed in the description of suitable nitrocompounds. Azoxybenzene, chloro-azoxybenzenes, alkyl and aryl substituted azobenzenes are particularly preferred.

The invention includes the use of any mixture of nitrocompounds, nitroso compounds, azo or azoxy-compounds.

It is preferred to use nitrocompounds rather than nitroso, azo or azoxy compounds.

When, in the practice of this invention, any of the above-mentioned nitrogen compounds; i.e., the nitro, nitroso, azo or azoxy compounds are used as the sole reacting nitrogen compound, the resulting ureas are the symmetrical 1,3-diarylureas, 1,3-dialkylureas, or substituted 1,3-diaryl or 1,3-dialkylureas. For exammple, when nitrobenzene is used as the only reacting nitrogen compound then carbanalide or 1,3-diphenylurea is the product. Likewise, p-methylnitrobenzene yields 1,3,-di-p-tolyurea and 3,4-dichloronitrobenzene yields 1,3-bis(3,4-dichlorophenyl) urea.

The process of this invention, however, is not limited to the production of symmetrical 1,3-dialkyl and 1,3-diaryl ureas. Addition of other suitable nitrogenous compounds in which the nitrogen is attached to one or more hydrogen atoms can result in unsymmetrical 1,3-dialkyl-, 1,3-diaryl-, 1,1-diaryl-3-aryl-, 1,1-dialkyl-3-aryl-, 1-alkyl-3-aryl- and 1,1-dialkyl-3-alkyl ureas. Suitable nitrogenous compounds in which the nitrogen atom is attached to one or more hydrogen atoms are generally the primary and secondary aromatic, aliphatic, aralkyl and cycloalkyl amines.

Generally, the amine group-containing compounds conform with one or the other of the general formula $R_1NH_2$; $R_1R_2NH$; $R'_1NH_2$, $R'_1R'_2NH$; $R_1R'_1NH$ wherein $R_1$ and/or $R_2$ may be the same or two different optionally substituted aliphatic, cycloaliphatic or araliphatic groups, preferably containing from 1 to 20 carbon atoms, or $R'_1$ and/or $R'_2$ may be the same or two different aromatic groups containing one or more benzenoid rings and preferably not more than 3 rings which can be fused or joined by single valency bonds, directly or through bridging groups which can be, for example, oxygen, nitrogen or sulfur atoms or sulfoxide, sulfone, amine, amide, or carbonyl groups, or alkylene groups in which, if desired, the carbon chain can be interrupted by, for example, oxygen or sulfur atoms, sulfoxide, sulfone or carbonyl groups, for example, methylene, oxymethylene, dimethylene sulfone or dimethylene ketone groups.

The group $R_1$ and $R_2$ can be alkyl, cycloalkyl, alkylene, cycloalkylene or aralkyl and the main carbon chain can, if desired, be interrupted, for example by oxygen, nitrogen or sulfur atoms,, sulfoxide, sulfone, amine, amide, carbonyl or carboxylic ester groups. The main chain can bear as substituents, for example, alkyl, alkoxy, aryl or aryloxy groups normally containing less than 10 carbon atoms. Especially suitable compounds of the type $R_1NH_2$ and $R_1R_2NH$ are those in which R is methyl, ethyl, n- and iso- propyl, n-, iso-, sec- and tert-butyl, amyl, hexyl, lauryl, cetyl, benzyl, chlorobenzyl, methoxybenzyl, cyclohexyl and in the case of the secondary amines $R_1R_2NH$ the R groups may be the same or any combination of the aforementioned groups.

Especially suitable compounds are primary and secondary amines of the type $R'_1NH_2$ and $R'_1R_2NH$ or those in which R is a benzenoid ring which can carry substituents, for example, alkyl and alkoxy groups containing up to 10 carbon atoms and halogen atoms such as phenyl, chlorophenyl, tolyl, xylyl, naphthyl, chloronaphthyl, pyridyl, chloropyridyl and in the case of secondary amines $R'_1R'_2NH$ the R groups may be the same or any combination of the aforementioned groups. The primary and secondary amines may contain from 1 to about 20 carbon atoms, but will usually contain from 1 to about 8 carbon atoms.

Examples of particularly suitable amines fitting the general formulas $R_1NH_2$, $R_1R_2NH$, $R'_1NH_2$, $R'_1R'_2NH$ and $R_1R'_1NH$ are methylamine, dimethylamine, ethylamine, diethylamine, propylamine, isopropylamine, dipropylamine, diisopropylamine, butylamine, dibutylamine, isobutylamine, diisobutylamine, amylamine, hexylamine, octylamine, cetylamine, cyclopropylamine, cyclobutylamine, cyclopentylamine, cyclohexylamine, cyclooctylamine, benzylamine, dibenzylamine, p-chlorobenzylamine, aniline, p-anisidine, p-toluidine, 3,4-dichloroaniline, m-chloroaniline, diphenylamine, 4,4''-dichlorodiphenylamine, N-methylethylamine, N-methylpropylamine, N-methylbutylamine, N-methylisobutylamine, N-ethylbutylamine, allylamine, N-methylcyclohexylamine, N-methylaniline, N-ethylaniline, N-allylaniline, N-methyl-4-chloroaniline and N-methyl-p-anisidine.

Thus, for example, using the above described amine and nitro compounds under the conditions of our invention the following ureas can be prepared: 3-(3,4-dichlorophenyl)-1,1-dimethylurea by reaction of 3,4-dichloronitrobenzene with dimethylamine; 1,1-dimethyl-3-phenylurea by reaction of nitrobenzene with dimethylamine, 3-(p-chlorophenyl)-1,1-dimethylurea by reaction of p-chloronitrobenzene with dimethylamine; and 1,1'-(4-methyl-m-phenylene)-bis[3-isopropylurea] by reaction of 2,4-dinitrotoluene with isopropylamine. Other combinations of amines and nitrocompounds can be used to obtain more or less readily the corresponding ureas. Such combinations are not limited to those amines and nitrocompounds described above and are apparent to one skilled in the art.

Catalysts for use in this invention include sulfur, selenium, sulfur compounds, selenium compounds and mixtures thereof. Selenium metal has been found to be as good as most selenium compounds and is conveniently handled in the powdered form. Other suitable selenium compounds are selenium dioxide, selenium trioxide, mixtures of these oxides titanium diselenide, selenium disulfide, sodium selenite, zinc selenite, sodium selenide, potassium selenide, potassium hydrogen selenide, hydrogen selenide, carbonyl selenide, barium selenide and organic selenium compounds. These compounds are not all of equivalent activity. Suitable sulfur compounds include sulfur itself, inorganic sulfides such as hydrogen sulfide, potassium hydrogen sulfide, potassium sulfide, sodium sulfide, carbonyl sulfide, aluminum sulfide, inorganic polysulfides such as ammonium polysulfide and organic sulfides and polysulfides having up to 20 carbon atoms such as diethylpolysulfide. Although sulfur oxides such as sulfur dioxide may be used, these oxides are reduced to sulfur under the conditions of the reaction.

The catalyst material, as indicated above, can be self-supported or can be deposited on an inert support or carrier for dispensing the catalyst to increase its effective surface. Alumina, silica, carbon, barium sulfate, calcium carbonate, organic ion exchange resins and analogous materials are useful as carriers for this purpose. A particular example of a supported catalyst is an ion exchange resin containing selenium as the cation and a sulfonic or carboxylic acid function as the anionic part of the resin, such as a selenium containing sulfonated macroporous styrene divinylbenzene resin. Selenium or sulfur containing molecular sieves can also be employed as well as complexes of selenium or sulfur with a ligand.

Base and water is preferably added to the reaction unless the primary or secondary amine is used as the base. Organic bases and metal carboxylic acid salts are effective. Organic bases suitable for the reaction include such amines as triethylamine, pyridine, quinoline, and n,n-dimethylaniline. Compounds normally considered as weak bases, such as the metal salts of carboxylic acids, sulfonic acids and phosphoric acid are preferred bases. Examples of such compounds and salts of other weak acids are lithium acetate, sodium acetate, potassium acetate, palladium acetate ruthenium acetate, the lithium salt of p-toluenesulfonic acid, the lithium salt of methyl sulfonic acid, lithium acid phosphate, the lithium salt of boric acid, calcium acetate sodium formate, lithium formate and antimony triacetate. The acid salts can be added preformed or can be made in the reaction mixture by adding appropriate quantities of corresponding base and acid. There is no limit on the type of acid used or the corresponding metal oxide or hydroxide employed. Thus, aliphatic, cycloaliphatic and aromatic acids, such as propionic, octanoic, cyclohexane carboxylic, benzoic, oxalic, malonic and the like can be employed. However, oxides or hydroxides of transition metal compounds tend to be more expensive than the alkali and alkaline earth metal hydroxides.

In those cases where unsymmetrical ureas are prepared by reaction of a nitrocompound with an amine the amine itself is often suitable as a base and no other additional basic compound need be added. Even so, there are some instances where addition of a base other than the reacting amine can be advantageous and, in such instances any of the above-described bases are suitable for this purpose.

While the process of the invention can typically be operated effectively in the absence of a solvent, a solvent can be employed. Aromatic solvents such as benzene, toluene, xylene; nitrile solvents such as acetonitrile and benzonitrile; amide type solvents such as N,N-dimethyl formamide and N,N-dimethyl acetamide; aliphatic, alicyclic or aromatic sulfoxide and sulfone solvents, such as dimethyl sulfoxide; aliphatic halogenated hydrocarbons such as 1,1,2-trichloro-1,2,2-trifluoroethane; halogenated aromatic hydrocarbons such as monochlorobenzene, dichlorobenzene and trichlorobenzene; ketones; esters; and ether solvents such as tetrahydrofuran, 1,4-dioxane, 1,2-dimethoxyethane and the like all can be employed as solvents. The ether compounds, for example, can be aliphatic, aromatic or heterocyclic, and they can also be either mono or polyethers, or combinations of these compounds.

Also suitable are the organic amines such as pyridine, triethylamine and the reactant primary and secondary amines used when unsymmetrical ureas are prepared. Combinations of tertiary amines can be used as can various combinations of tertiary amines with primary or secondary reactant amines.

The invention is carried out with at least molar amounts of reactants, i.e., nitrocompound, amine and carbon monoxide.

Preferably, however, a molar excess of the amine compound or the nitrocompound or both are present but, generally, in the case of preparing the unsymmetrical ureas, a molar excess of the amine is used.

The mole ratio of the nitrocompound to the catalyst can vary over a wide range i.e. from 5:1 to 2000:1; however, a somewhat more preferred range of moles of nitrocompound to the catalyst is 5:1 to 1000:1. It will be understood that with reference to the moles of catalyst it is meant the element selenium or sulfur and not the moles of the form in which the catalyst is charged.

Similarly, with respect to the amount of base employed the mole ratio (based on equivalent nitrogroups) can vary from 50:1 to 1:10 of the nitrocompound to the base. When the desired products are unsymmetrical 1,3-ureas which require the reaction of an amine with a nitrocompound in many cases the reacting amine can also serve as the base. When this is the case the mole ratio of nitrocompound to base may be well outside the limits described above without any detrimental effect on the reaction.

When symmetrical 1,3-ureas are the desired product by reaction of the nitrocompound, the presence of water can be advantageous. Thus, the mole ratio of water to catalyst, i.e. S or Se, can range from as little as about 0.5:1 to as much as 1000:1 or more. Such water can be added separately or produced "in situ," for example, when a base such as potassium hydroxide and an acid such as acetic acid are employed in equivalent molar amounts to give the weakly basic compound potassium acetate and water in equi-molar amounts.

The order of mixing the reactants is not critical and can be varied within the limitations of the equipment employed. A simple procedure is to charge the nitrogenous compound (or compounds), catalyst, base and/or water into the reaction vessel, introduce the proper amount of carbon monoxide and then heat the mixture to obtain the desired reaction. A suitable pressure vessel, such as an autoclave, which is preferably provided with heating means and agitation means, such as a stirrer or an external rocking mechanism, is employed for the reaction.

Generally, the amount of carbon monoxide in the free space of the reactor is sufficient to maintain the desired pressure as well as to provide a reactant for the process. As the reaction progresses additional carbon monoxide can be fed to the reactor either intermittently or continuously. Although greater and lesser amounts of carbon monoxide can be employed if desired, generally the total amount of carbon monoxide added during the reaction is between about 3 and about 50 moles and preferably between about 8 and about 15 moles of carbon monoxide per non-cyclic group in which the nitrogen atom of the nitrogenous organic compound is directly attached to a single carbon atom and is also attached by a double bond to an oxygen or another nitrogen atom. The highest carbon monoxide requirements are generally utilized in a process in which carbon monoxide is added continuously, but suitable recycle of carbon monoxide containing gas streams greatly reduces the overall consumption of carbon monoxide.

The reaction temperature is generally maintained in the range of about 50° to about 250° C. and preferably within the range of from about 100 to about 200° C. These temperature ranges permit a convenient rate of reaction to be achieved while avoiding undesirable side reactions. It will be understood, however, that any elevated temperatures below that at which the starting materials or the products decompose can be used. The reaction is carried out, as indicated above, at superatmospheric pressures which is normally between about 10 and 200 atmospheres, although higher or lower reaction pressures can be employed if other reaction conditions are suitably adjusted. Preferably, however, only moderate carbon monoxide pressures in the range of about 10 to about 100 atmospheres are employed and the reaction is conveniently run at a temperature of below about 200° C. within this pressure range.

While the reaction of the present invention is normally carried out batchwise, if desired, the reaction can be carried out semi-continuously or even continuously. Ion exchange type catalysts, for example, are particularly suited for continuous reactions. The reaction time is dependent upon the nature of the reactants, temperature, pressure and the type of catalyst employed, as well as the type of equipment which is used. Normally the reaction time is less than 180 minutes and generally the effectiveness of the catalysts of this invention permits the reaction to be completed within a time period between about ten minutes and about 120 minutes.

After the reaction has been completed, the temperature of the reaction mixture can be dropped to ambient temperature and the pressure vessel vented. The reaction product is then treated by conventional procedures, including filtration, distillation, or other suitable separation techniques, to effect separation of urea from unreacted starting material, solvent, byproduct, catalyst, etc.

The invention is further illustrated by, but not limited to, the following examples.

The reactions set forth in these examples were all run in 316 Stainless Steel shaking autoclaves. It will be understood, however that less expensive forms of stainless steel can be used and that if desired equivalent reaction vessels, such as glasslined vessels, can be employed. Conversions and yields reported in the examples were determined by gas chromatographic analysis and by isolation of the product. The ureas were purified by recrystallization and the infrared spectra and melting points obtained.

EXAMPLE I

Ten milliliters of nitrobenzene, 100 milliliters of water were charged into a 300 milliliter rocking autoclave along with 1.0 grams of selenium metal (gray powder) and 1.0 grams of sodium acetate. The autoclave was flushed with nitrogen and carbon monoxide and finally pressured to 800 psig with carbon monoxide. After heating to 150° C. for one hour the autoclave was cooled, vented and the contents analyzed. A 66.3 percent conversion of nitrobenzene resulted with a 33.8 percent yield of purified carbanalide.

EXAMPLE II

Example I was repeated at 180° C. using 0.5 grams water. A 48.9 percent conversion resulted with a 57.7% yield of pure carbanalide.

EXAMPLE III

The autoclave was charged with 13.7 grams of 4-nitrotoluene, 100 milliliters of tetrahydrofuran, 1.0 grams of sodium acetate, 1.0 grams of selenium metal and 0.5 milliliters of water. After flushing with nitrogen and carbon monoxide it was pressured to 800 psig with carbon monoxide and heated to 180° C. for one hour. After cooling and venting analysis indicated a 61.0 percent conversion and a yield of pure 1,3-di-p-tolylurea of 45.9 percent.

EXAMPLE IV

Similarly, 15.3 grams of 4-nitroanisole was reacted along with 100 milliliters of tetrahydrofuran, 1.0 grams selenium metal, 1.0 gram sodium acetate and 0.5 milliliters of $H_2O$ at an initial carbon monoxide pressure of 800 l psig. After one hour at 180° C. a 68 percent conversion was obtained giving a 44.1 percent yield of pure 1,3-bis (4-methoxyphenyl) urea.

EXAMPLE V

To a 300 milliliter racking autoclave were charged 10 milliliters of nitrobenzene, 50 milliliters of tetrahydrofuran, 50 milliliters of triethylamine, 0.5 gram water and 1.5 grams selenium dioxide. The autoclave was sealed, pressured to 800 psig with carbon monoxide and heated to 150° C. for one hour. Analysis of the reaction mixture showed a 97.1 percent conversion of nitrobenzene with a 67.3 percent yield of carbanalide.

EXAMPLE VI

Ten milliliters of nitrobenzene, 100 milliliters of tetrahydrofuran, 1.0 gram sulfur and 1.0 gram of sodium acetate trihydrate were charged to the autoclave. After pressuring to 800 psig with carbon monoxide it was heated to 180° C. for one hour. Analysis of the reaction solution by high speed liquid chromatography showed a carbanalide yield of 3.4 per cent.

EXAMPLE VII

Ten milliliters of nitrobenzene, 50 milliliters of tetrahydrofuran, 50 milliliters of triethylamine, 0.5 gram water and 1.0 gram sulfur were charged to the autoclave which was then pressured to 500 psig with carbon monoxide and heated to 200° C. for 1 hour. Analysis of the reaction solution showed a 7.7 percent yield of carbanalide.

EXAMPLE VIII

The autoclave was charged with 10 milliliters of nitrobenzene, 50 milliliters of tetrahydrofuran, 50 milliliters of triethylamine, 0.5 grams of water and 1.3 grams $H_2S$. The autoclave was then pressured to 500 psig with carbon monoxide and heated to 200° C. for 1 hour. A carbanalide yield of 3.9 percent was found.

EXAMPLE IX

To a 300 milliliter autoclave were charged 5.0 grams of azobenzene, 50 milliliters of tetrahydrofuran, 50 milliliters of triethylamine, 0.5 gram water and 1.0 gram of gray selenium powder. The autoclave was pressured to 800 psig with carbon monoxide and heated to 170° C. for 1 hour. Analysis of the reaction solution by high speed liquid chromatography showed a carbanalide yield of 4.4 percent.

The following Examples demonstrate the use of this invention to prepare unsymmetrical ureas by reaction of a nitro compound with an amine.

EXAMPLE X

Ten milliliters of nitrobenzene, 100 milliliters of tetrahydrofuran, 1.0 gram potassium acetate, 1.0 gram selenium metal and 9.0 grams of dimethylamine are charged to the autoclave. The autoclave is flushed and pressured to 800 l psig with carbon monoxide and heated to 180° C. for 1 hour. After reaction 1,1-dimethyl-3-phenylurea is obtained.

EXAMPLE XI

Ten milliliters of nitrobenzene, 100 milliliters of tetrahydrofuran, 1.0 gram potassium acetate, 1.0 gram selenium and 21.4 grams of p-toluidine are charged to the autoclave which is then flushed and pressured to 800 psig with carbon monoxide. The temperature is raised to 180° C. for one hour giving 1-p-tolyl-3-phenylurea as product.

EXAMPLE XII

Five milliliters of nitrobenzene, 14.3 grams diethylamine, 50 milliliters of tetrahydrofuran, 50 milliliters of triethylamine and 1.0 gram gray selenium powder were charged to the autoclave. After pressuring to 800 psig with carbon monoxide it was heated to 150° C. for one hour. Analysis of the reaction by high speed liquid chromatography showed a yield of 1,1-diethyl-3-phenylurea of 75.5 percent based on nitrobenzene. A small amount of carbanalide was also found.

EXAMPLE XIII

Five milliliters of nitrobenzene, 12.3 grams of para-anisidine, 50 milliliters of tetrahydrofuran, 50 milliliters of triethylamine and 1.0 gram of gray selenium powder were charged to the autoclave. After pressuring to 500 psig with carbon monoxide it was heated to 150° C. for 1 hour. Analysis of the reaction solution showed the unsymmetrical 1-phenyl-3-(p-anisyl) urea at a 34.4 percent yield based on nitrobenzene.

We claim:

1. A method for the production of ureas which comprises contacting at elevated temperatures and pressures in a basic solution a nitrogenous organic compound selected from the group consisting of organic nitro, nitroso, azo and azoxy compounds containing up to 24 carbon atoms, with carbon monoxide and water in the presence of an active amount of a catalyst selected from the group consisting of sulfur, hydrogen sulfide, carbonyl sulfide, potassium hydrogen sulfide, potassium sulfide, sodium sulfide, aluminum sulfide, ammonium sulfide, diethyl polysulfide and mixtures thereof.

2. The method as claimed in claim 1 wherein said nitro compound is a nitro aromatic compound.

3. The method as claimed in claim 2 wherein said nitro aromatic compound is nitrobenzene.

4. The method as claimed in claim 2 wherein said nitro aromatic compound is a nitrotoluene.

5. The method as claimed in claim 2 wherein said nitro aromatic compound is 4-nitroanisole.

6. The method as claimed in claim 2 wherein said nitro compound is a tertiary nitroaliphatic compound.

7. The method as claimed in claim 1 wherein said catalyst is sulfur.

8. The method as claimed in claim 1 wherein said temperature is in the range of from 50° to 250° C. and said pressure is in the range of from 10 atmospheres to 200 atmospheres.

9. A method for the production of ureas which comprises contacting at elevated temperatures and pressures in a basic solution an organic nitro aromatic compound containing up to 24 carbon atoms with carbon monoxide and water in the presence of an active amount of a catalyst selected from the group consisting of sulfur, hydrogen sulfide, carbonyl sulfide, potassium hydrogen sulfide, potassium sulfide, sodium sulfide, aluminum sulfide, ammonium sulfide, diethyl polysulfide and mixtures thereof.

10. The method as claimed in claim 9 wherein said nitro aromatic compound is a nitrobenzene.

11. The method as claimed in claim 9 wherein said nitro aromatic compound is a nitrotoluene.

12. The method as claimed in claim 9 wherein said catalyst is sulfur.

* * * * *